(12) United States Patent
Seyfried

(10) Patent No.: US 7,005,654 B2
(45) Date of Patent: Feb. 28, 2006

(54) METHOD FOR MICROSCOPY, AND MICROSCOPE

(75) Inventor: Volker Seyfried, Nussloch (DE)

(73) Assignee: Leica Microsystems Heidelberg GmbH, Mannheim (DE)

( * ) Notice: Subject to any disclaimer, the term of this patent is extended or adjusted under 35 U.S.C. 154(b) by 212 days.

(21) Appl. No.: 10/601,804

(22) Filed: Jun. 23, 2003

(65) Prior Publication Data

US 2004/0065845 A1    Apr. 8, 2004

(30) Foreign Application Priority Data

Jun. 25, 2002    (DE) .................... 102 28 374

(51) Int. Cl.
*G01N 21/64* (2006.01)

(52) U.S. Cl. .................. 250/458.1; 250/459.1; 250/461.1; 250/462.1

(58) Field of Classification Search ........... 250/458.1, 250/459.1, 461.1, 461.2; 359/368, 370, 371, 359/385, 386, 388

See application file for complete search history.

(56) References Cited

U.S. PATENT DOCUMENTS

| | | | |
|---|---|---|---|
| 3,973,129 A * | 8/1976 | Blumberg et al. ....... | 250/461.2 |
| 5,034,613 A * | 7/1991 | Denk et al. ............. | 250/458.1 |
| 5,731,588 A | 3/1998 | Hell et al. .............. | 250/458.1 |
| 5,777,732 A | 7/1998 | Hanninen et al. ....... | 356/318 |
| 5,835,262 A * | 11/1998 | Iketaki et al. ........... | 359/352 |
| 6,094,274 A * | 7/2000 | Yokoi .................... | 356/417 |
| 6,326,605 B1 * | 12/2001 | Modlin et al. .......... | 250/214 SW |
| 6,855,941 B1 * | 2/2005 | Tomioka ................. | 250/483.1 |
| 6,859,313 B1 * | 2/2005 | Iketaki et al. ........... | 359/385 |

FOREIGN PATENT DOCUMENTS

| | | |
|---|---|---|
| DE | 4414940 | 11/1995 |
| WO | 9521393 | 8/1995 |
| WO | 0004352 | 1/2000 |

OTHER PUBLICATIONS

A. M. Weiner: "Femtosecond pulse shaping using spatial light modulators", Review of Scientific Instruments, vol. 71, No. 5, May 2000, pp. 1929-1960.

* cited by examiner

*Primary Examiner*—David Porta
*Assistant Examiner*—Christopher Webb
(74) *Attorney, Agent, or Firm*—Davidson, Davidson & Kappel, LLC

(57) ABSTRACT

The invention discloses a method for microscopy in which a specimen is illuminated with pulsed illuminating light that comprises light from a spectral region, and detection light proceeding from the specimen is detected in a detection spectral region. The method is characterized in that the detection spectral region lies within the spectral region, and that the illuminating light contains no light from the detection spectral region or at least none having the same polarization properties. A microscope is additionally disclosed.

8 Claims, 6 Drawing Sheets

METHOD FOR MICROSCOPY, AND MICROSCOPE

CROSS REFERENCE TO RELATED APPLICATIONS

Priority is claimed to German patent application 102 28 374.5, the subject matter of which is hereby incorporated by reference herein.

FIELD OF THE INVENTION

The invention concerns a method for microscopy.

The invention furthermore concerns a microscope and a confocal scanning microscope.

BACKGROUND OF THE INVENTION

For the investigation of biological specimens, it has been usual for some time to prepare the specimen using optical markers, in particular fluorescent dyes. Often, for example in the field of genetic research, several different fluorescent dyes are introduced into the specimen and become attached specifically to certain specimen constituents. From the fluorescence properties of the prepared specimen conclusions can be drawn, for example, as to the nature and composition of the specimen or the concentration of certain substances within the specimen.

In scanning microscopy in particular, methods that exploit location-dependent nonlinearities of the specimen are used. This field includes, for example, coherent anti-Stokes Raman scattering (CARS), which is known inter alia from PCT Application WO 00/04352 A1. It must be noted, however, that illuminating light having at least two different illuminating light wavelengths, at high light power levels, is required for this method.

Another method that makes use of nonlinear effects is so-called STED (stimulated emission depletion) microscopy, known for example from PCT/DE/95/00124. Here the lateral edge regions of the focus volume of the excitation light beam are illuminated with a light beam of another wavelength, called the stimulation light beam, that is emitted by a second laser, so that the specimen regions excited there by the light of the first laser are brought back to the ground state in stimulated fashion. Only the light spontaneously emitted from the regions not illuminated by the second laser is then detected, resulting overall in improved resolution.

In multi-photon scanning microscopy, the fluorescent photons attributable to a two-photon or multi-photon excitation process are detected. The probability of a two-photon transition depends on the square of the excitation light power level, and therefore occurs with high probability at the focus of the scanning illuminating light beam, since the power density is highest there. To achieve sufficiently high light power levels, it is useful to pulse the illuminating light and thereby achieve high peak pulsed light power levels. This technique is known, and is disclosed e.g. in U.S. Pat. No. 5,034,613 "Two-photon laser microscopy" and in German Unexamined Application DE 44 14 940. A further advantage of multi-photon excitation especially in confocal scanning microscopy lies in the improved bleaching behavior, since the specimen bleaches out only in the region of sufficient power density, i.e. at the focus of an illuminating light beam. Outside that region, in contrast to one-photon excitation, almost no bleaching takes place.

In scanning microscopy, a specimen is illuminated with a light beam in order to observe the reflected or fluorescent light emitted from the specimen. The focus of an illuminating light beam is moved in a specimen plane by means of a controllable beam deflection device, generally by tilting two mirrors, the deflection axes usually being perpendicular to one another so that one mirror deflects in the X direction and the other in the Y direction. Tilting of the mirrors is brought about, for example, by means of galvanometer positioning elements. The power level of the light coming from the specimen is measured as a function of the position of the scanning beam. The positioning elements are usually equipped with sensors to ascertain the present mirror position.

In confocal scanning microscopy specifically, a specimen is scanned in three dimensions with the focus of a light beam.

A confocal scanning microscope generally comprises a light source, a focusing optical system with which the light of the source is focused onto an aperture (called the "excitation pinhole"), a beam splitter, a beam deflection device for beam control, a microscope optical system, a detection pinhole, and the detectors for detecting the detected or fluorescent light. The illuminating light is coupled in via a beam splitter. The fluorescent or reflected light coming from the specimen travels back through the beam deflection device to the beam splitter, passes through it, and is then focused onto the detection pinhole behind which the detectors are located. Detection light that does not derive directly from the focus region takes a different light path and does not pass through the detection pinhole, so that a point datum is obtained which results, by sequential scanning of the specimen, in a three-dimensional image. A three-dimensional image is usually achieved by acquiring image data in layers, the track of the scanning light beam on or in the specimen ideally describing a meander (scanning one line in the X direction at a constant Y position, then stopping the X scan and slewing by Y displacement to the next line to be scanned, then scanning that line in the negative X direction at constant Y position, etc.). To allow acquisition of image data in layers, the specimen stage or the objective is displaced after a layer has been scanned, thus bringing the next layer to be scanned into the focal plane of the objective.

Spectral influencing of light pulses by amplitude modulation or phase modulation is known from the literature, e.g. from Rev. of Scientific Instruments 71 (5) pp. 1929–1960. Spectral modification of the laser pulses is usually used to shorten the pulses, to shape them optimally, or to control optically induced processes.

The aforesaid methods are disadvantageous in that high light power levels are necessary, resulting on the one hand in great demands on the light source and on the other hand in undesirable damage to the specimen, for example due to bleaching.

SUMMARY OF THE INVENTION

It is therefore an object of the invention to provide a method for microscopy that reliably and efficiently allows exploitation of nonlinear processes with reduced specimen damage.

The invention provides a method comprising the following steps:
  generating pulsed illuminating light that comprises wavelengths which lie in a spectral region;
  defining a detection spectral region that lies within the spectral region;

influencing the light components of the illuminating light that comprise wavelengths within the detection spectral region;

illuminating a specimen with the illuminating light;

detecting the detection light proceeding from the specimen within the detection spectral region.

A further object of the invention is to provide a microscope which reliably and efficiently allows an investigation of a specimen exploiting nonlinear processes with reduced specimen impact.

The invention also provides a microscope having a light source for generating pulsed illuminating light that comprises light from a spectral region, and having at least one detector for detecting the detection light proceeding from a specimen in a detection spectral region, wherein the detection spectral region lies within the spectral region; and the illuminating light contains no light from the detection spectral region having the same polarization properties.

The invention has the advantage that the method according to the present invention exploits location-dependent optical nonlinearities but makes do with much lower light intensities, the use of the lowest possible light intensities having particular significance especially for biological specimens. Investigation of the specimen to a great depth is also possible.

An aspect of the method according to the present invention is to influence, certain spectral components (specifically those from the detection spectral region) from the spectrum of ultrashort laser pulses (i.e. preferably picosecond and femtosecond laser pulses); to focus the illuminated light prepared in this fashion onto a specimen volume; and to detect in practically background-free fashion the detection light thereby produced, by nonlinear processes, in the region of the previously removed spectral components. The power level and (optionally) spectral distribution of this detection light is used for image production.

In a preferred embodiment, the influencing is a removal of the light components of the illuminating light that comprise wavelengths within the detection spectral region. In another embodiment, the influencing contains a modification of the polarization state of the light components of the illuminating light that comprise wavelengths within the detection spectral region. The modification of the polarization state can encompass, in particular, a rotation of a linear polarization. Rotation of the linear polarization direction makes the detection light in the detection spectral region distinguishable from the illuminating light.

In another preferred embodiment, the influencing encompasses a spectral filtration. Provided for this purpose, in an embodiment, is a spectral filter that removes from the illuminating light the light components of the illuminating light that comprise wavelengths within the detection spectral region. In this embodiment, the illuminating light contains no light from the detection spectral region. In another variant, a spectral filter is provided that modifies the polarization state of the light components of the illuminating light that comprise wavelengths within the detection spectral region.

The spectral filtration removes certain frequency regions from the spectrum of the illuminating light in order to create there a spectral window within which detection light produced as a result of nonlinear processes can be detected in background-free fashion.

In a preferred embodiment, a further spectral filter is provided that allows only light of the wavelengths of the detection spectral region to arrive at the detector. The further spectral filter is preferably inverse with respect to the spectral filter.

In an embodiment, the illuminating light is already generated in such a way that the detection spectral region lies within the spectral region, and so that the illuminating light contains no light from the detection spectral region. The detection spectral region or regions can, for example, be the spectral gaps between the equidistant modes of a mode-coupled pulsed laser.

In another embodiment, the microscope is a scanning microscope, in particular a confocal scanning microscope.

BRIEF DESCRIPTION OF THE DRAWINGS

The subject matter of the invention is depicted schematically in the drawings and will be described below with reference to the Figures, identically functioning elements being labeled with the same reference characters. In the drawings.

DETAILED DESCRIPTION OF THE INVENTION

Figure 1:
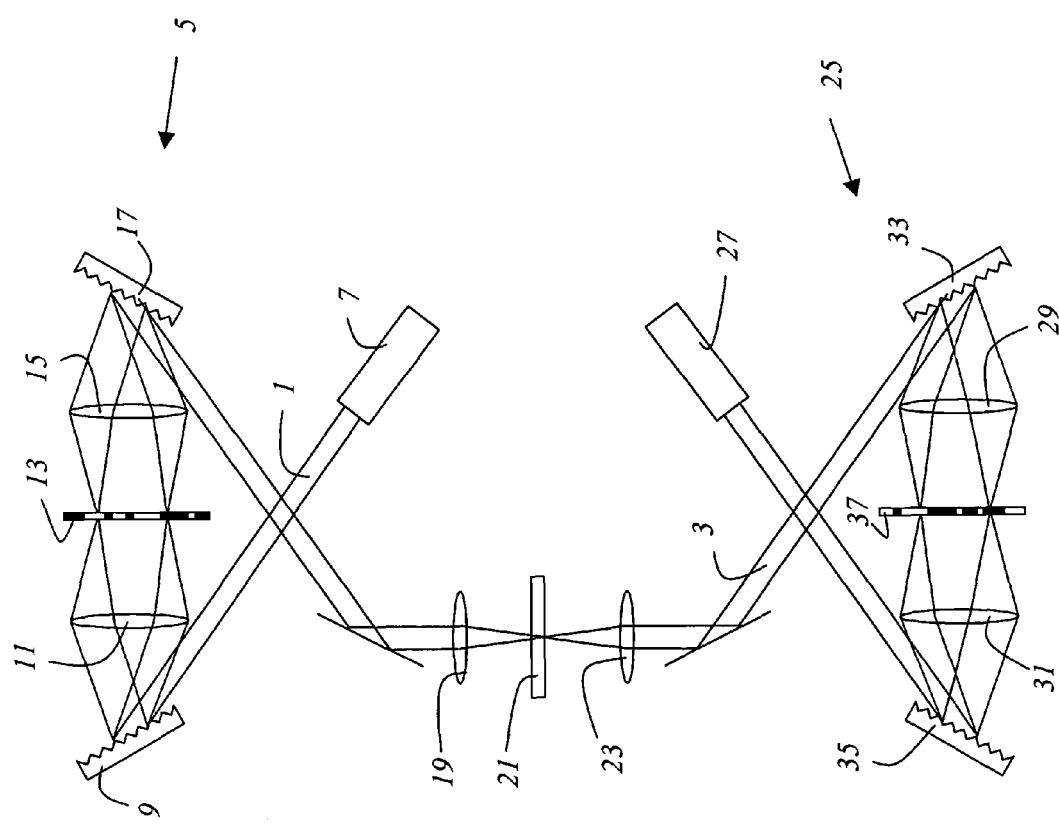
FIG. 1 shows a microscope according to the present invention.
Figure 2A:
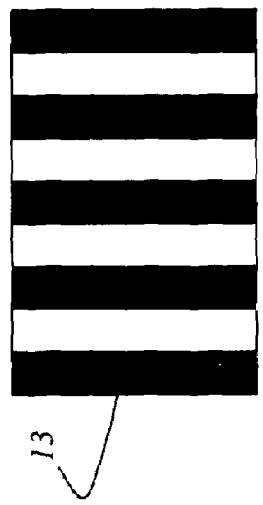
FIG. 2 shows masks for spectral filters.
Figure 2B:
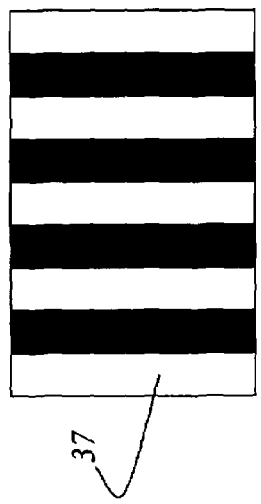
Figure 2C:
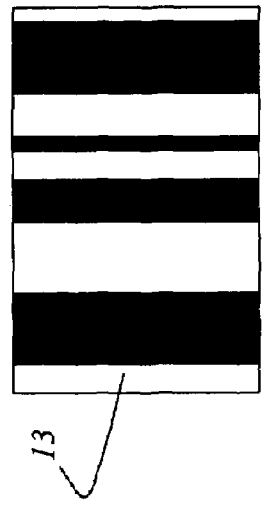
Figure 2D:
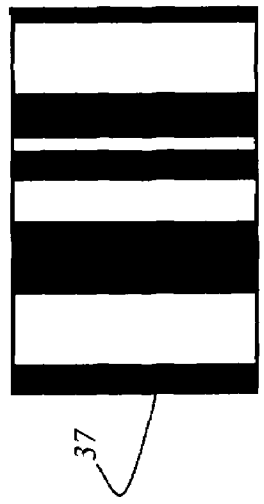

FIG. 1 schematically shows a microscope according to the present invention that is embodied as a scanning microscope. The optical components for guiding, directing, and focusing illuminating light beam 1 (generated by a pulsed laser 7) and detection light beam 3, and the apparatuses for evaluating the detection light data and displaying an image of the specimen, are not shown in the interest of better clarity. These components are sufficiently familiar to one skilled in the art.

The microscope contains a spectral filter 5 that removes from illuminating light beam 1 the light components of the illuminating light that comprise wavelengths within the detection spectral region. For that purpose, the light is spatially spectrally split using a first grating 9, and then focused with first lens 11 onto a mask 13 which removes the spectral components that lie within the detection spectral region. Grating 9 and first mask 13 are located in the focal planes of lens 11 in a 4f arrangement. Mask 13 has transparent and opaque regions. It can be expressed as a static mask but also as a dynamically controllable mask (liquid crystal display, hinged mirror array). After first mask 13, the various spectral components of the illuminating light are combined again, by means of a symmetrical arrangement of a second lens 15 and second grating 17, into a common illuminating light beam 1. This illuminating light beam is then coupled into the microscope beam path and focused by an objective 19 onto specimen 21 that is to be examined. The microscope scans, for example, by the fact that one or more mirrors in the beam path are embodied as scanning mirrors, and/or by moving the specimen stage. In the interior of specimen 21 at the location of the focus of illuminating light beam 1, nonlinear processes such as self-phase modulation, continuum generation, etc. take place, in which new light frequencies are generated that may also be present, inter alia, in the regions filtered out by the previous stop. After passage through the specimen, detection light beam 3 proceeding from specimen 21 is collimated by a condenser 23 and directed to a further spectral filter 25. Further spectral filter 25 is embodied inversely with respect to spectral filter 5 through which illuminating light beam 1 passes; i.e. wherever light previously passed through, the light is now blocked. It contains a third lens 29 and a fourth lens 31, as well as a third grating 33 and a fourth grating 35; also a second mask 37 that is the inverse of first mask 13. The components of illuminating light beam 1 still present in detection light beam 3 are thereby filtered out, so that ultimately only detection light produced at the specimen focus arrives at detector 27. The power level of this light provides information, inter alia, about the nonlinear refractive indices at the specimen focus which depend on local conditions in specimen 21, and is therefore suitable, as the focus is scanned over specimen 21, as a signal for image-producing methods.

FIG. 2 shows several spatial first masks 13 and second masks 37 that can be used in first spectral filter 5 and in second spectral filter 25, second masks 37 being inverse with respect to first masks 13. The transmitting regions can be limited even further.

Figure 3:
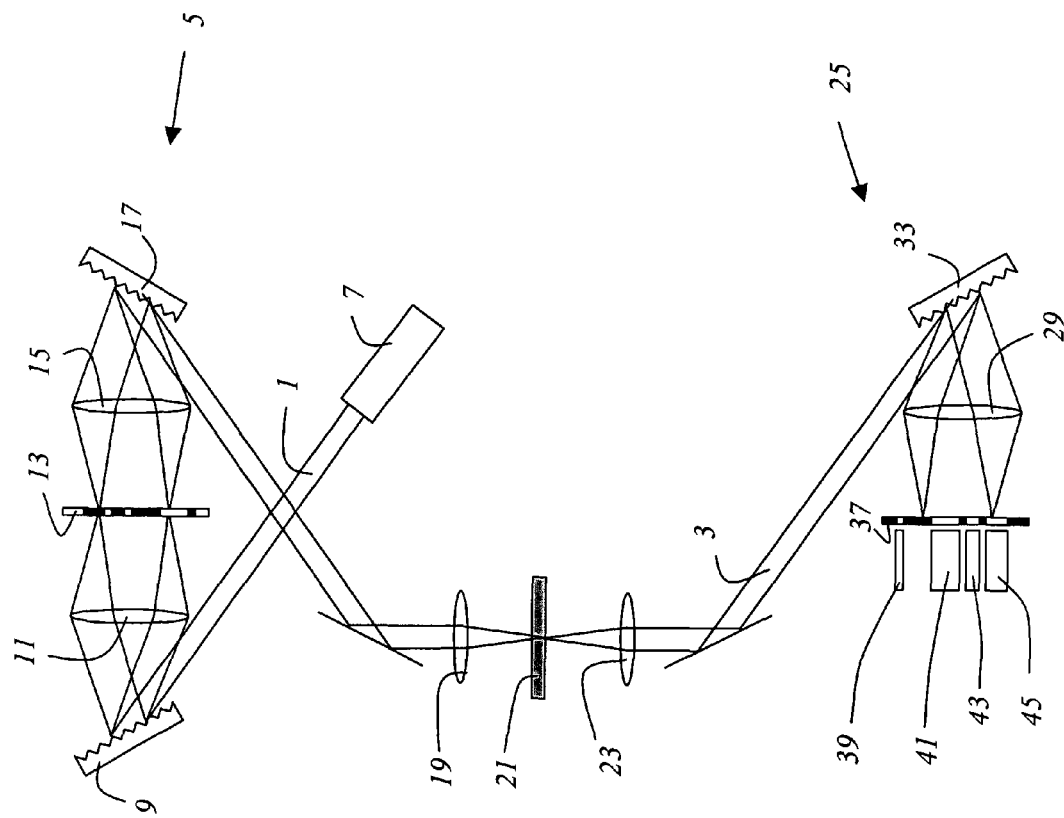
FIG. 3 shows a further microscope according to the present invention.

FIG. 3 shows a further microscope according to the present invention. It corresponds analogously, in terms of illumination, to the scanning microscope shown in FIG. 1; several detectors 39, 41, 43, 45 arranged behind second mask 37 are provided for detection. A linear detector or an array of detectors (e.g. CCD) could also be used. After spectral splitting using grating 33, the components of detection light beam 3 that comprise the same wavelength region as the components of illuminating light beam 1 that were removed by first mask 13 strike the several individual detectors 39, 41, 43, 45. In a particularly simple arrangement, the mask itself can even be omitted. Because the several detectors 39, 41, 43, 45 are used, additional information is obtained as to the intensity with which the nonlinear processes are occurring in the various spectral regions; this can possibly be utilized for differentiated image production.

It is also possible to use for second spectral filter 25 at least some of the same optical elements as for first spectral filter 13, by guiding the light beam through at least some of them a second time.

Figure 4:
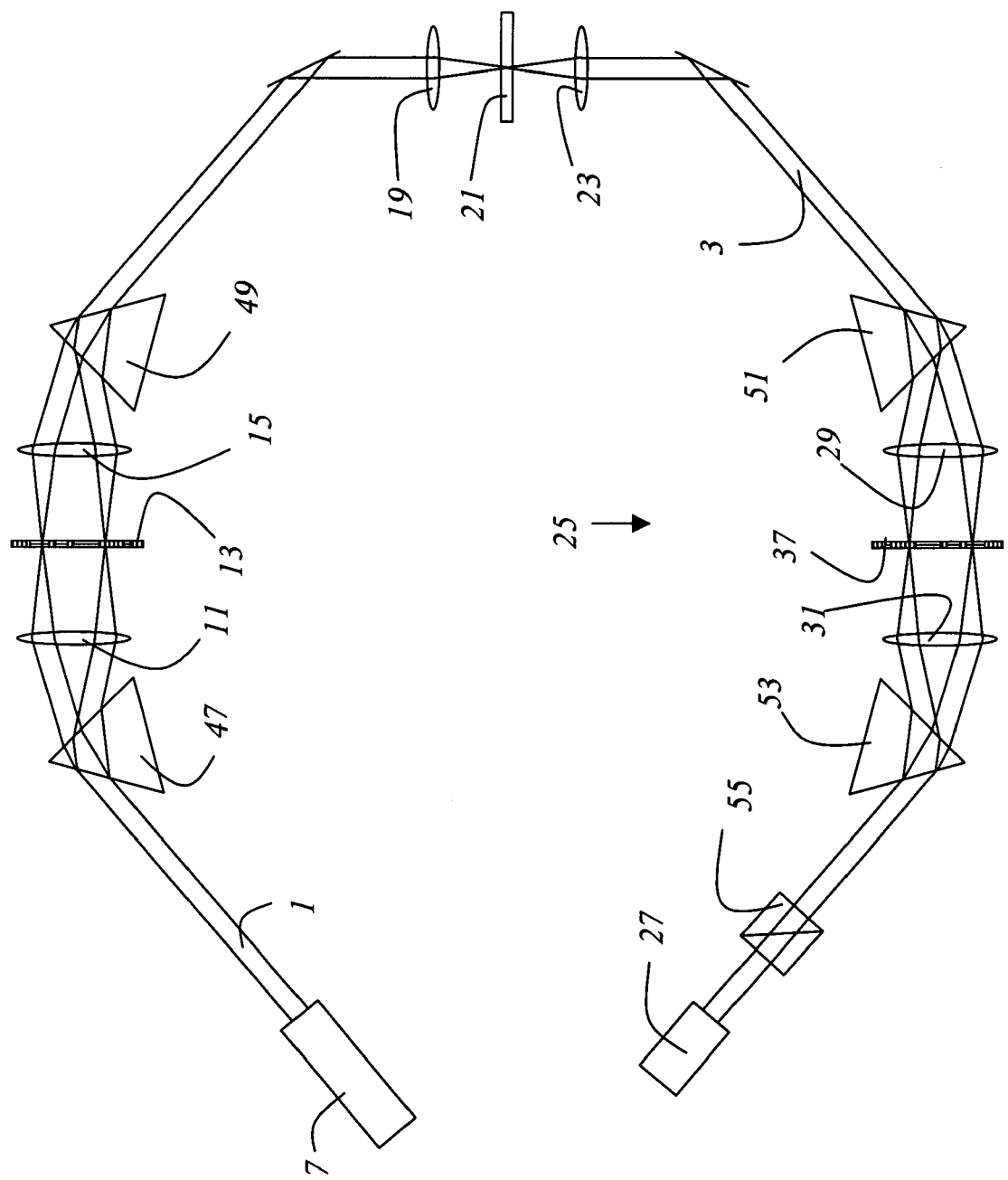
FIG. 4 shows a further microscope according to the present invention.

FIG. 4 shows a further microscope according to the present invention. Instead of gratings 9, 17, 33, 35, a first prism 47, second prism 49, third prism 51, and fourth prism 53 are used for spectral splitting and combining. Illuminating light beam 1 generated by pulsed laser 7 is linearly polarized. Mask 13 rotates through 90 degrees the polarization direction of those components of illuminating light beam 1 that comprise wavelengths from the detection regions. The polarization influence is exerted by way of a suitably patterned and oriented birefringent fixed mask 13 (e.g. patterned λ/2 plate), or also by means of a dynamically controlled mask 13 that can be implemented, for example, using a liquid crystal display. After passage through the specimen, the detection light proceeding from the specimen is filtered through a second spectral filter 25 in such a way that the illuminating light whose polarization was not rotated by first spectral filter 5 is completely removed. This is done by the fact that in second spectral filter 25, by way of a suitable second mask 37, the polarization state of the various spectral components is modified in such a way that all components deriving directly from pulsed laser 7 are once again given a common polarization, which is removed from the beam path by means of a downstream polarizer 55. In the concrete exemplary embodiment, those spectral components that had already experienced a polarization change in first spectral filter 13 are once again rotated 90° in polarization in second spectral filter 25. Polarizer 55 then removes from the beam all spectral components that have a polarization of 0°. The beam path then, as a rule, contains only light which was produced in the specimen by nonlinear processes, and whose intensity permits conclusions as to the local nonlinear refractive indices of the specimen at the focus and is therefore suitable for image production. In this exemplary embodiment it is also possible to dispense with certain parts of second spectral filter 25 (e.g. fourth lens 31 and fourth prism 53) if, for example, the detector(s) is/are equipped with polarizers and is/are arranged directly behind mask plane 25.

Figure 5:
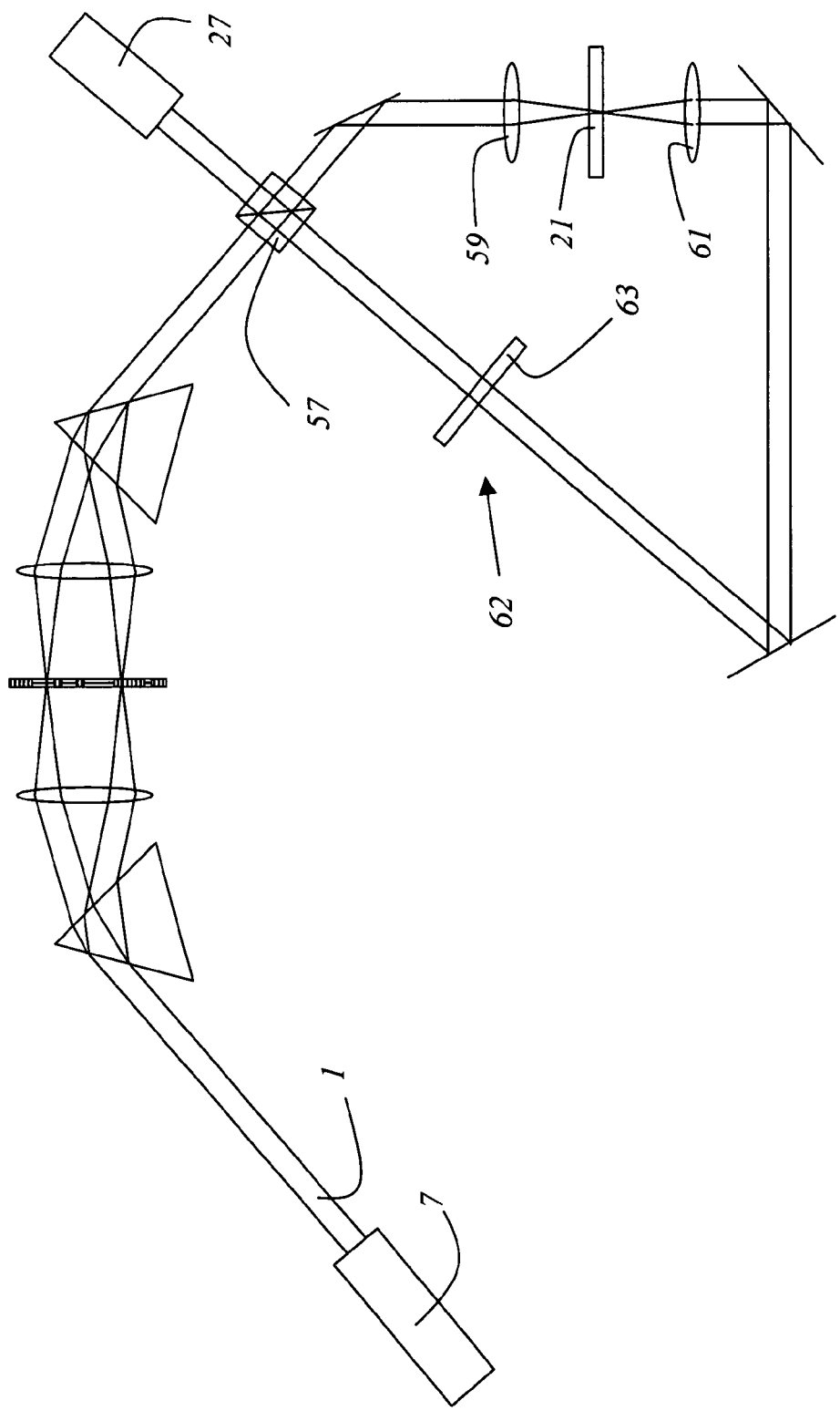
FIG. 5 shows a further microscope according to the present invention.

FIG. 5 shows an embodiment in which the light polarized in the 0° or 90° direction (depending on wavelength) is split upstream from the specimen using a polarization splitter 57, after which the two light components of illuminating light beam 1 are focused from opposite directions onto specimen 21 by a first objective 59 and a further objective 61. Here the objective for the one polarization direction is in each case simultaneously the condenser for the other polarization direction. After passage through the specimen and through a polarization rotator 62 (this number has already been assigned to the second objective, including in the Figure), which is embodied as a λ/2 plate 63 that preferably rotates the polarization 90°, the two light components of the detection light are combined using the polarizing beam splitter; the light uninfluenced by the specimen is separated, by polarizing beam splitter 57, from the light later to be detected in such a way that only the light just produced in the specimen is detected in detector 27.

Figure 6:
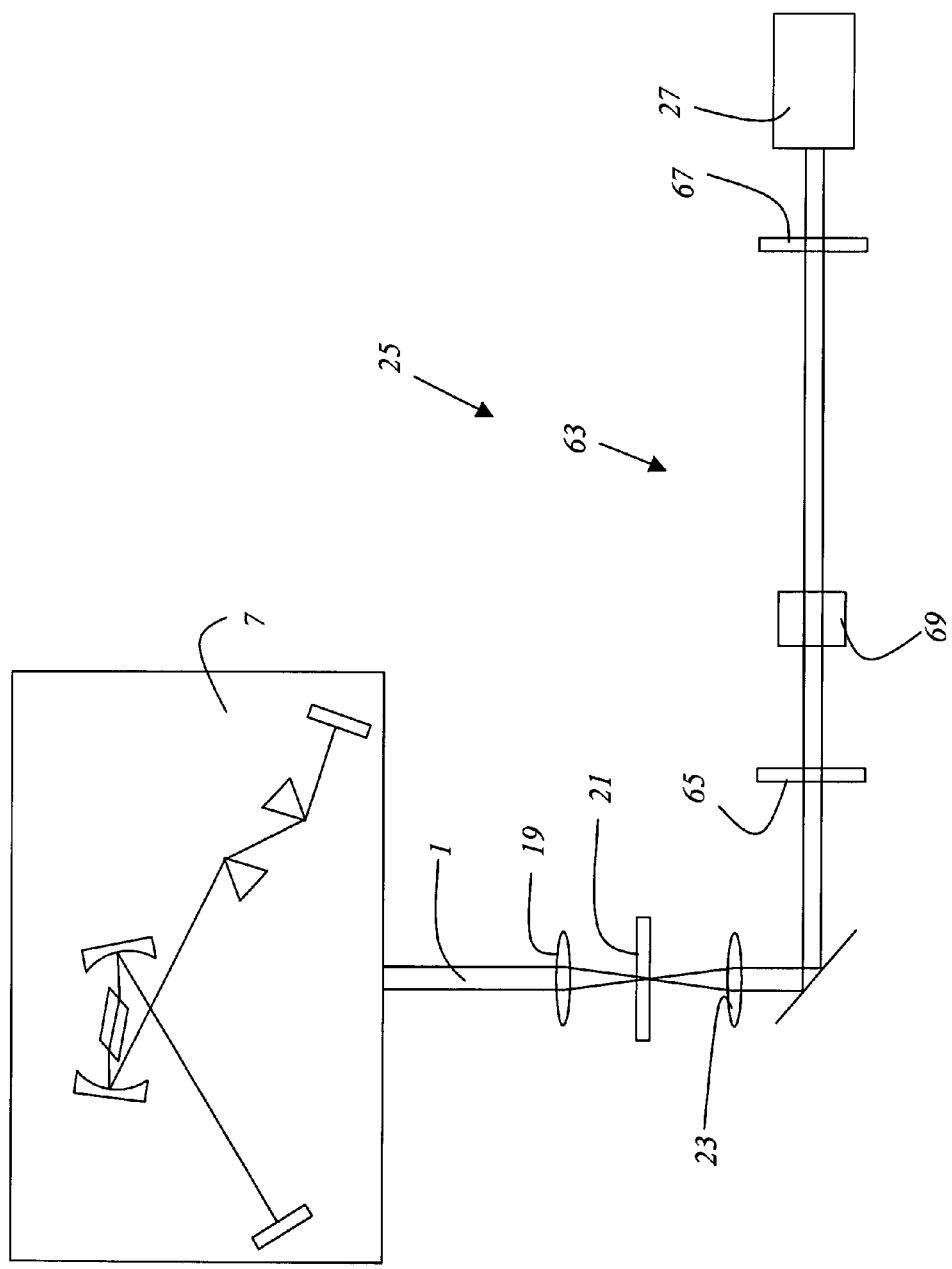
FIG. 6 shows a further microscope according to the present invention.

In the exemplary embodiment in FIG. 6, the first spectral filter has been omitted. The light of pulsed laser 7 is made up of lines lying very close together. This occurs in many usual picosecond and femtosecond lasers as an effect of mode coupling. The spectral line spacing usually corresponds here to the pulse frequency of the laser in question; for example, the spectrum of a titanium-sapphire femtosecond laser pulsing at a repetition rate of 80 MHz is made up of individual spectral lines at a spectral spacing of 80 MHz. Gaps in the spectrum are present between the individual spectral lines, so that the spectrum of this pulsed laser 7 is similar to the filtered spectra of the exemplary embodiments discussed previously. If components are present in these spectral regions after an excitation laser of this kind has passed through specimen 21, this is attributable to nonlinear processes; as in the case of the previous exemplary embodiments, this can be utilized for image production. Separation of the detection light produced by nonlinear processes from the excitation light can be accomplished, as in the previous exemplary embodiments, by spatial filtration; in this context, the use of monochromators, etc. of course also represents a spatial filtration. Alternatively and in particularly preferred fashion, what is used as second spectral filter 25 is an etalon 63, which is constituted by a first mirror 65 and a second mirror 67 and which removes from detection light beam 3 all spectral components within a certain wavelength spacing (as is also possible, in the previous exemplary embodiments, with a suitable first spectral filter). In the case of the mode-coupled laser, the spectral distance within which etalon 63 absorbs light must correspond exactly to the spectral spacing of the individual laser modes, which substantially means that the length of etalon 63 must be matched to the effective resonator length of the mode-coupled laser. Since the etalon length is relatively long for the short-pulse lasers commonly in use at present, etalon 63 is usually embodied as a resonator made up substantially of two semitransparent mirrors 65, 67 at the spacing of the effective resonator length. It is useful if there is located, in the interior of the resonator, a controllable element 69 with which the effective resonator length can be regulated so that precise adaptation can be performed and with which any drift resulting e.g. from thermal longitudinal expansion can be controlled out. An element of this kind could be made of materials whose refractive index can be controlled externally, e.g. liquid crystals or ferroelectric crystals. Appropriate regulation of the etalon's resonator length could also be accomplished by way of a movable end mirror. Instead of the resonator length of the etalon, the length of the short-pulse laser resonator could, of course, also be regulated.

The invention has been described with reference to exemplary embodiments. It is self-evident, however, that changes and modifications can be made without thereby leaving the range of protection of the claims below.

What is claimed is:

1. A method for microscopy comprising the steps of:
    generating pulsed illuminating light that comprises wavelengths which lie in a spectral region;
    defining a detection spectral region that lies within the spectral region;
    influencing the light components of the illuminating light that comprise wavelengths within the detection spectral region by removing the light components using a spectral filter so as to provide influenced illuminating light;
    illuminating a specimen with the influenced illuminating light;
    detecting the detection light proceeding from the specimen within the detection spectral region; and
    allowing, using a further spectral filter, only light of the wavelengths of the detection spectral region to arrive at the detector, the further spectral filter being inverse with respect to the spectral filter.

2. The method as defined in claim 1, wherein the influencing includes a modification of the polarization state of the light components of the illuminating light that comprise wavelengths within the detection spectral region.

3. The method as defined in claim 2, wherein the modification of the polarization state encompasses a rotation of a linear polarization.

4. The method as defined in claim 1, wherein a pulsed laser is provided for generating the pulsed illuminating light.

5. A microscope having a light source for generating pulsed illuminating light that comprises light from a spectral region, and having at least one detector for detecting the detection light proceeding from a specimen in a detection spectral region, wherein the detection spectral region lies within the spectral region;
    further comprising a spectral filter that removes, from the illuminating light, light components of the illuminating light that comprise wavelengths within the detection spectral region, and further comprising a further spectral filter that allows only light of the wavelengths of the detection spectral region to arrive at the detector, wherein the further spectral filter is inverse with respect to the spectral filter.

6. The microscope as defined in claim 5, further comprising a third spectral filter that modifies the polarization state of the light components of the illuminating light that comprise wavelengths within the detection spectral region.

7. A confocal scanning microscope having a light source for generating pulsed illuminating light that comprises light from a spectral region, and having at least one detector for detecting the detection light proceeding from a specimen in a detection spectral region, wherein the detection spectral region lies within the spectral region;
    further comprising a spectral filter that removes, from the illuminating light, light components of the illuminating light that comprise wavelengths within the detection spectral region, and further comprising a further spectral filter that allows only light of the wavelengths of the detection spectral region to arrive at the detector, wherein the further spectral filter is inverse with respect to the spectral filter.

8. The confocal scanning microscope as defined in claim 7, further comprising a third spectral filter that modifies the polarization state of the light components of the illuminating light that comprise wavelengths within the detection spectral region.

* * * * *